United States Patent [19]

Mori et al.

[11] Patent Number: 4,892,944

[45] Date of Patent: Jan. 9, 1990

[54] PROCESS FOR PRODUCING QUATERNARY SALTS

[75] Inventors: Shoichiro Mori; Kazuhiko Ida; Makoto Ue, all of Ibaraki, Japan

[73] Assignee: Mitsubishi Petrochemical Co., Ltd., Tokyo, Japan

[21] Appl. No.: 192,524

[22] Filed: May 11, 1988

[30] Foreign Application Priority Data

| May 13, 1987 | [JP] | Japan | 62-116463 |
| May 14, 1987 | [JP] | Japan | 62-117380 |
| May 22, 1987 | [JP] | Japan | 62-125427 |
| May 22, 1987 | [JP] | Japan | 62-125428 |

[51] Int. Cl.$^4$ ............................................. C07C 85/24
[52] U.S. Cl. .................................. 544/107; 544/108; 564/282; 564/289; 564/290; 564/291; 564/296; 568/9; 568/17
[58] Field of Search ............... 564/292, 289, 290, 291, 564/296; 544/107, 108; 568/9, 17

[56] References Cited

U.S. PATENT DOCUMENTS 4,634,509 1/1987 Shimizu et al. .................. 204/182.4
4,776,929 10/1988 Aoyama et al. .................. 204/59 R

FOREIGN PATENT DOCUMENTS 60-100690 3/1987 Japan .
63-024080 4/1988 Japan .
63-119214 4/1988 Japan .

OTHER PUBLICATIONS

Chem. Abstracts, vol. 106, No. 19 (1987); Abst. No. 155960u.

*Primary Examiner*—Joseph Paul Brust
*Assistant Examiner*—MarySue Howard
*Attorney, Agent, or Firm*—Oblon, Spivak, McClelland, Maier & Neustadt

[57] ABSTRACT

A process for producing quaternary salts of high purity is disclosed, comprising reacting a tertiary amine or phosphine with a carbonic acid diester to form a corresponding quaternary carbonate and further mixing it with an acid to perform decarboxylation. The quaternary salts thus obtained are useful compounds which can be used in wide fields as various catalysts, electrolytes, additives, medicaments, etc.

8 Claims, No Drawings

PROCESS FOR PRODUCING QUATERNARY SALTS

FIELD OF THE INVENTION

This invention relates to a process for producing quaternary salts of high purity efficiently. More particularly, the invention relates to a process for producing a quaternary ammonium salt or a quaternary phosphonium salt by reacting a tertiary amine or phosphine with a carbonic acid diester to form a corresponding quaternary carbonate and further mixing it with an acid to perform decarboxylation.

The quaternary salts obtained by the process of this invention are useful compounds which are used in wide fields as various catalysts such as a phase transfer catalyst, etc., electrolytes for aqueous or organic electrolytic solutions, various additives, medicaments, etc.

BACKGROUND OF THE INVENTION

As a synthesis process for a quaternary salt such as, for example, a quaternary ammonium salt, a process of quaternarizing a tertiary amine with an alkyl halide or a dialkylsulfuric acid under heating has been employed.

For example, when an alky halide is used as a quaternarization reagent, the quaternarization reaction is shown by the following equation:

$$R_3N + R'X \rightarrow R_3R'N^\oplus X^\ominus (X: halogen)$$

Further, in the case of producing quaternary ammonium salts having various different anions, anion exchange of quaternary ammonium halides (e.g., chlorides, bromides, and iodides) have been usually employed.

In the case of an anion exchange reaction of a quaternary ammonium halide, a process, in equilibrium, shown in the following equation is known:

$$R_3R'N^\oplus X^\ominus + H^\oplus A^\ominus \rightleftarrows R_3R'N^\oplus A^\ominus + H^\oplus X^\ominus$$

wherein $A^\ominus$ is an anion being exchanged.

When $H^\oplus A^\ominus$ being exchanged is a strong acid, the equilibrium is deviated to the right side of the aforesaid equation and hence the desired anion exchange reaction can be sufficiently progressed, but, when $H^\oplus A^\ominus$ is a weak acid such as an organic acid, it is very difficult to perform the anion exchange reaction to be completed.

As other process, a process of reacting a quaternary ammonium halide with an alkali metal salt or an alkaline earth metal salt and a process of reacting a quaternary ammonium halide with a silver salt may be considered. However, in these processes, it is considerably difficult to completely remove raw material anions from the desired quaternary ammonium salt thus obtained, and hence, these processes are unsuitable to produce a quaternary ammonium salt of high purity. And, the process of using a silver salt is expensive and hence unsuitable as an industrial process.

From the aforesaid view points, as a process for producing a quaternary ammonium salt of high purity, a process of once converting a quaternary ammonium halide into a quaternary ammonium hydroxide (Reaction a), and then, neutralizing the hydroxide with an acid corresponding to the anion of the desired salt (Reaction b) as shown in the following equation is most general:

$$R_3R'N^\oplus X^\ominus \rightarrow R_3R'N^\oplus OH^\ominus \text{(Reaction a)}$$

$$R_3R'N^\oplus OH^\ominus + H^\oplus A^\ominus \rightarrow R_3R'N^\oplus A^\ominus + H_2O$$
(Reaction b)

As the process for producing quaternary ammonium hydroxide by aforesaid Reaction a, various processes are known such as; for example, in the case of using a bromide, are known reacting a quaternary ammonium bromide dissolved in a suitable solvent with a quaternary ammonium hydroxide type ion exchange resin, reacting a quaternary ammonium bromide with an alkali metal oxide in a liquid medium, separating bromide ions as $Br_2$ by an electrochemical method to provide the hydroxide, and using a silver compound.

However, these processes are all expensive as an industrial process and, in particular, in the case of producing a high-pure product wherein the content of halide in the quaternary ammonium hydroxide is controlled to an order of ppm, the production cost becomes considerably high.

The aforesaid matters are same in the case of producing quaternary phosphonium salts. That is, as a process of synthesizing a quaternary phosphonium salt, quaternarizing a tertiary phosphine with an alkyl halide, a dialkylsulfuric acid, etc., under heating as shown in the equation:

$$R_3P + R'X \rightarrow R_3R'P^\oplus X^\ominus (X: halogen)$$

and then performing, in equilibrium, an anion exchange by the reaction shown in the following equation is generally known:

$$R_3R'P^\oplus X^\ominus + H^\oplus A^\ominus \rightleftarrows R_3R'P^\oplus A^\ominus + H^\oplus X^\ominus$$

Also, as a process for producing a high pure quaternary phosphonium salt, a process of once converting a quaternary phosphonium halide into a quaternary phosphonium hydroxide (Reaction a') and then neutralizing the hydroxide with an acid corresponding to the anion of the desired salt (Reaction b') as shown in the following equations is most general:

$$R_3R'P^\oplus X^\ominus \rightarrow R_3R'P^\oplus OH^\ominus \text{(Reaction a')}$$

$$R_3R'P^\oplus OH^\ominus + H^\oplus A^\ominus \rightarrow R_3R'P^\oplus A^\ominus + H_2O$$
(Reaction b')

Furthermore, the processes for producing the quaternary phosphonium hydroxide by aforesaid Reaction a' are expensive as an industrial process same as in the aforesaid cases of producing a quaternary ammonium hydroxide and, in particular, in the case of producing a high-pure product wherein the halide content in the quaternary phosphonium hydroxide is controlled to an order of ppm, the production cost also becomes considerably high.

SUMMARY OF THE INVENTION

An object of this invention is to provide a novel process capable of producing a high-pure quaternary salt efficiently as compared with conventional processes of once producing a quaternary ammonium or phosphonium hydroxide.

Other object of this invention is to provide a novel technique capable of producing a high-pure quaternary salt even in the case that the desired product is a salt of a relatively weak acid such as an organic acid.

Thus, according to this invention, there is provided a process for producing a quaternary salt comprising (a) a 1st step of reacting a tertiary amine or a phosphine with a carbonic acid diester to produce a quaternary ammonium or phosphonium carbonate, and (b) a 2nd step of mixing the quaternary carbonate formed with an acid, while removing carbon dioxide generated from the system, to anion-exchange the quaternary carbonate into the corresponding acid.

DETAILED DESCRIPTION OF THE INVENTION

As the tertiary amine which is a raw material in this invention, there are aliphatic amines such as trimethylamine, triethylamine, ethyldimethylamine, tri-n-propylamine, tri-n-butylamine, tri-n-octylamine, diethyl-i-propylamine, N,N,N',N'-tetramethylethylenediamine, etc.; alicyclic amines such as N-methylpyrrolidine, N-ethylpyrrolidine, N-methylpiperidine, N-ethylpiperidine, N-n-butylpiperidine, N-methylhexamethyleneimine, N-ethylhexamethyleneimine, N-methylmorpholine, N-butylmorpholine, N,N'-dimethylpiperazine, N,N'-diethylpiperazine, 1,5-diazabicyclo[4,3,0]-5-nonene, 1,8-diazabicyclo[5,4,0]-7-undecene, etc.; and nitrogen-containing heterocyclic aromatic compounds such as pyridine, 4-dimethylaminopyridine, picolines, N-methylimidazole, N-methylbenzimidazole, quinoline, 4,4'-dipyridyl, etc.

As the tertiary phosphine which is a raw material in this invention, there are saturated aliphatic phosphines such as trimethylphosphine, diethylmethylphosphine, triethylphosphine, tri-n-propylphosphine, tri-n-butylphosphine, tri-n-pentylphosphine, tri-i-butylphosphine, di-n-butylmethylphosphine, tricyclohexylphosphine, 1,2-bis(dimethylphosphine)ethane, etc.; unsaturated aliphatic phosphines such as triarylphosphine, etc.; aromatic phosphines such as triphenylphosphine, tribenzylphosphine, di-n-propylphosphine, diethylphenylphosphine, n-butyl-diphenylphosphine, etc.; and cyclic phosphines such as 1-ethylphosphoran, 1-phenylphosphoran, 1-phenylphosphane, 1-phenylphosphepane, etc.

As the carbonic acid diester, there are dimethyl carbonate, ethylmethyl carbonate, diethyl carbonate, dipropyl carbonate, etc., but a carbonic acid diester having an alkyl moiety of small carbon atom number such as dimethyl carbonate is preferred since, in this case, the quaternarization reaction proceeds fast.

The quaternarization reaction which is the 1st step in this invention is performed using a tertiary amine or a phosphine and a carbonic acid diester in a mol ratio of from 0.2 to 5, and preferably from 0.3 to 3, in the presence or absence of a solvent, at reaction temperature of from 20° C. to 200° C., and preferably from 30° C. to 160° C.

When a tertiary amine and dimethyl carbonate are used as the raw materials, the reaction occurring is shown by the following equation:

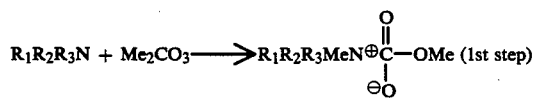

wherein $R_1R_2R_3$ represents a hydrocarbon residue of the tertiary amine.

Usually, when the tertiary amine or phosphine is sufficiently converted into a quaternarized product, distilling off the unreacted amine or phosphine and the unreacted carbonic acid diester together with the solvent, in the case of using a solvent, is performed, and the product, if necessary, recrystallized from a suitable organic solvent is then sent to the 2nd step.

In the 2nd step, a stoichiometric amount or a little excessive amount of an acid having the anion of the desired salt as a conjugated base is usually added dropwise to the quaternary carbonate in the presence or absence of a solvent and carbon dioxide generated is removed from the system under reduced pressure or by blowing an inert gas into the reaction system.

In the case of using quaternary ammonium methylcarbonate, the reaction occurring is shown by the following equation:

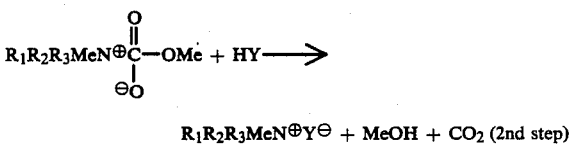

wherein Y represents a conjugated base of the acid being used.

There is no particular restriction on the acid being used in the 2nd step, but a stronger acid as compared to carbonic acid completes faster the anion exchange. However, even in the case of using an acid similar to carbonic acid or weaker than carbonic acid, the anion exchange can be carried out by removing the carbonate as carbon dioxide in the system to shift the equilibrium.

Specific examples of the inorganic acid are HF, HCl, HBr, HI, $HNO_3$, $H_2SO_4$, $H_3PO_3$, $H_3BO_4$, $HClO_4$, $HBF_4$, $HPF_6$, $HSbF_6$, $HAsF_6$, $HOSO_2Cl$, $HOSO_2F$, $H_2CrO_4$, $H_2S_2O_6$, $HMnO_4$, $HReO_4$, $H_2SeO_4$, HSCN, etc.

In the quaternary salts obtained, the salts having $BF_4^-$, $PF_6^-$, $ClO_4^-$, *etc., as the conjugated base are preferred.*

In this invention, a desired high-pure quaternary salt is obtained even in the case of using a relatively weak acid such as an organic acid, which makes the process of this invention advantageous.

Specific examples of the organic acid are aliphatic monocarboxylic acids such as formic acid, acetic acid, propionic acid, butyric acid, valeric acid, caproic acid, enanthic acid, caprylic acid, pelargonic acid, capric acid, undecanic acid, lauric acid, tridecanic acid, myristic acid, pentacanic acid, palmitic acid, heptadecanic acid, stearic acid, nonadecanic acid, arachidic acid, isobutyric acid, isovaleric acid, isocaproic acid, ethylbutyric acid, methylvaleric acid, isocaprylic acid, propylvaleric acid, ethylcaproic acid, isocapric acid, tuberculostearic acid, pivalic acid, 2,2-dimethylbutanic acid, 2,2-dimethylpentanic acid, 2,2-dimethylhexanic acid, 2,2-dimethylheptanic acid, 2,2-dimethyloctanic acid, 2-methyl-2-ethylbutanic acid, 2-methyl-2-ethylpentanic acid, 2-methyl-2-ethylhexanic acid, 2-methyl-2-ethyljeptanic acid, 2-methyl-2-propylpentanic acid, 2-methyl-2-propylhexanic acid, 2-methyl-2-propylheptanic acid, acrylic acid, crotonic acid, isocrotonic acid, 3-butenic acid, pentenic acid, hexenic acid, heptenic acid, octenic acid, nonenic acid, decenic acid, undecenic acid, dodecinic acid, tuzuic acid, physteric acid, goshuyuic acid, palmitoleic acid, petroselinic acid, oleic acid, elaidic acid, vaccenic acid, gadoleic acid, methacrylic acid, 3-methylcrotonic acid, tiglic acid, methylpentenic acid, cyclopentacarboxylic acid, cyclohexanecarboxylic acid, trifluoroacetic acid, phenylacetic acid, chloroacetic acid, glycoric acid, lactic acid, etc.; aliphatic polycarboxylic acids such as citric acid, malonic acid, succinic acid, glutaric acid, adipic acid, pimelic acid, suberic acid, azelaic acid, sebacic acid, undecane diacid, dodecane diacid, tridecane diacid, tetradecane diacid, pentadecane diacid, hexadecane diacid, heptadecane diacid, octadecane diacid, noncadecane diacid, eicosane diacid, methylmalonic acid, ethylmalonic acid, propylmalonic acid, butylmalonic acid, pentylmalonic acid, hexylmalonic acid, dimethylmalonic acid, methylethylmalonic acid, diethylmalonic acid, methylpropylmalonic acid, methylbutylmalonic acid, ethylpropylmalonic acid, dipropylmalonic acid, ethylbutylmalonic acid, propylbutylmalonic acid, dibutylmalonic acid, methylsuccinic acid, ethylsuccinic acid, 2,2-dimethylsuccinic acid, 2,3-dimethylsuccinic acid, 2-methylglutaric acid, maleic acid, citraconic acid, itaconic acid, methyleneglutaric acid, monomethyl maleate, 1,5-octanedicarboxylic acid, 5,6-decanedicarboxylic acid, 1,7-decanedicarboxylic acid, 4,6-dimethyl-4-nonene-1,2-dicarboxylic acid, 4,6-dimethyl-1,2-nonanedicarboxylic acid, 1,7-dodecanedicarboxylic acid, 5-ethyl-1,10-decanedicarboxylic acid, 6-methyl-6-dodecene-1,12-dicarboxylic acid, 6-methyl-1,12-dodecanedicarboxylic acid, 6-ethylene-1,12-dodecanedicarboxylic acid, 7-methyl-7-tetradecene-1,14-dicarboxylic acid, 7-methyl-1,14-tetradecanedicarboxylic acid, 3-hexyl-4-decene-1,2-dicarboxylic acid, 3-hexyl-1,12-decanedicarboxylic acid, 6-ethylene-9-hexadecene- 1,16-dicarboxylic acid, 6-ethyl-1,16-hexadecanedicarboxylic acid, 6-phenyl-1,12-dodecanedicarboxylic acid, 7,12-dimethyl-7,11-octadecanediene-1,18-dicarboxylic acid, 7,12-dimethyl-1,18-octadecanedicarboxylic acid, 6,8-diphenyl-1,14-tetradecanedicarboxylic acid, 1,1-cyclopentanedicarboxylic acid, 1,1-cyclopentanedicarboxylic acid, 1,2-cyclopentanedicarboxylic acid, 1,1-cyclohexanedicarboxylic acid, 1,2-cyclohexanedicarboxylic acid, 4-cyclohexene-1,2-dicarboxylic acid, 5-nobornene-2,3-dicarboxylic acid, malic acid, glutamic acid, tartaric acid, citric acid, etc.; aromatic monocarboxylic acids (including o-, m-, and p-isomers) such as benzoic acid, toluic acid, ethylbenzoic acid, propylbenzoic acid, isopropylbenzoic acid, butylbenzoic acid, sec-butylbenzoic acid, tert-butylbenzoic acid, hydroxybenzoic acid, anisic acid, ethoxybenzoic acid, propoxybenzoic acid, isopropoxybenzoic acid, butoxybenzoic acid, isobutoxybenzoic acid, sec-butoxybenzoic acid, tert-butoxybenzoic acid, aminobenzoic acid, N-methylaminobenzoic acid, N-ethylaminobenzoic acid, N-propylaminobenzoic acid, N-isopropylaminobenzoic acid, N-butylaminobenzoic acid, N-isobutylaminobenzoic acid, N-sec-butylaminobenzoic acid, N-tert-butylaminobenzoic acid, N,N-dimethylaminobenzoic acid, N,N-diethylaminobenzoic acid, nitrobenzoic acid, fluorobenzoic acid, resorcinic acid, etc.; aromatic polycarboxylic acids such as phthalic acid, isophthalic acid, terephthalic acid, nitrophthalic acid, trimellitic acid, hemimellitic acid, trimesic acid, pyromellitic acid, etc., and phenols such as phenol, p-fluorophenol, β-naphthol, o-nitrophenol, p-nitrophenol, p-aminophenol, catechol, resorcin, 2-chlorophenol, 2,4-dichlorophenol, 4,4'-dihydroxydiphenyl-2,2-propane, etc.

In the quaternary salts obtained, those having the anion of a dicarboxylic acid such as maleic acid, phthalic acid, etc., as the conjugated base are preferred.

After the reaction is over, a by-produced alcohol and, if a solvent is used, the solvent are distilled off to provide a desired quaternary salt as solids. If necessary, by recrystallizing the product from a suitable solvent, a high-pure product can be obtained.

Also, when a little excessive amount of an acid to the stoichiometric amount is used for completely removing the carbonic acid ions, the excess acid can be removed by a treatment such as recrystallization, etc.

In the case of producing a quaternary salt of a carboxylic acid in the process of this invention, a carboxylic acid anhydride can be used as the acid in the 2nd step. In this case, it sometimes happens that the quaternary salt having a sufficient purity is not obtained, since a carboxylic acid alkyl ester is formed.

Accordingly, by dissolving the quaternary methyl carbonate obtained in the 1st step using dimethyl carbonate as the carbonic acid diester in water, after removing methanol formed from the system, and mixing the solution with a carboxylic acid anhydride, while removing carbon dioxide generated from the system, a corresponding carboxylate can be produced at high purity without forming the methyl ester.

There is no particular restriction on the carboxylic acid anhydride but specific examples thereof are aliphatic monocarboxylic acid anhydride such as acetic anhydride, propionic anhydride, etc.; aliphatic dicarboxylic acid anhydrides such as maleic anhydride, citraconic anhydride, 1,2-cyclohexanedicarboxylic anhydride, etc.; and aromatic polycarboxylic acid anhydrides such as phthalic anhydride, nitrophthalic anhydride (including 3-nitro compound and 4nitro compound), trimellitic anhydride, pyromellitic anhydride, etc.

As the quaternary salts obtained, those from a dibasic acid anhydride such as maleic anhydride, phthalic anhydride, etc., are preferred.

In the case of producing a quaternary ammonium salt, the reaction occurring in this case is shown by the following equation:

$$R_4N^+MeCO_3^- + H_2O \rightleftharpoons R_4N^+HCO_3^- + MeOH \qquad (1)$$

$$R_4N^+HCO_3^- + HAn \rightarrow R_4N^+A^- + CO_2 \qquad (2)$$

wherein HAn represents a carboxylic acid anhydride and A represents a conjugated base thereof.

In the process, the quaternary methyl carbonate is first dissolved in water and after shifting the equilibrium of equation (1) to the right side by removing MeOH formed from the system, the solution is mixed with a carboxylic acid anhydride to cause the reaction as shown in equation (2).

In this case, the step of removing MeOH from the reaction system is performed in the existence of water at reaction temperature of from 0° C. to 200° C., preferably from 20° C. to 80° C. under reduced pressure or normal pressure.

The amount of water is usually from 0.1 to 100, and preferably from 0.5 to 10 by weight based on the amount of the quaternary methyl carbonate.

It is desirable to remove MeOH to an extent that the content of MeOH becomes less than 11%, and preferably less than 6.0% to the amount of the quaternary bicarbonate.

Also, in the reaction step with a carboxylic acid anhydride, a stoichiometric amount or a little excess amount of the carboxylic acid anhydride is mixed with a quaternary bicarbonate in the existence of water and carbon dioxide generated at reaction temperature of from 0° C. to 200° C., and preferably from 20° C. to 80° C. is removed from the system under reduced pressure or normal pressure.

The mixing of a carboxylic acid anhydride is performed by adding dropwise an aqueous solution of a quaternary bicarbonate (95 wt % to 0.1 wt %, and preferably from 70 to 10 wt %) to a suspension of the carboxylic acid anhydride in water of from 0.5 to 100, and preferably 1 to 10 by weight ratio to the anhydride, or adding the carboxylic acid anhydride alone or a mixture of the carboxylic acid anhydride and water of from 0.01 to 100 by weight ratio to an aqueous solution of a quaternary bicarbonate (95 to 0.1 wt %, and preferably 70 to 10 wt %).

After the reaction is over, the solvent is distilled off to provide the desired quaternary carboxylate as solids. If necessary, by recrystallizing the product from a suitable solvent, a high-pure product can be obtained.

As described above, according to the process of this invention, various kinds of quaternary ammonium salts and quaternary phosphonium salts can be efficiently produced and also even in the case of using a relatively weak acid such as an organic acid, the desired products can be obtained at high purity, which is the large feature of this invention.

Then, the invention is explained in more practically by the following examples.

EXAMPLE 1

(1st Step)

In a stirring system autoclave were filled 17.8 g of dimethyl carbonate, 20.0 g of triethylamine, and 20.0 g of methanol as solvent and they were reacted for 12 hours at reaction temperature of 115° C. and at reaction pressure of 5.0 kg/cm$^2$G. After the reaction, the autoclave was cooled and the reaction product was collected and analyzed by gas chromatograph. The results showed that the conversion of triethylamine was 94.6% and the amount of solid after distilling off unreacted materials and solvent was 34.0 g (89.9% of the theoretical value). From the elemental analysis and H-NMR, it was confirmed that the product was triethylmethylammonium methyl carbonate.

(2nd Step)

In 15 g of water was dissolved 10.0 g of triethylmethylammonium methyl carbonate and 8.8 g of an aqueous solution of 60% HClO$_4$ was gradually added to the solution. Simultaneously with the addition thereof, carbon dioxide generated vigorously. For more completely removing carbon dioxide, degassing was performed for 2 hours at 40° C. and 20 mmHg and after confirming carbonate ions being less than 20 ppm by ion chromatography, water was distilled off. The residue was recrystallized from 9.5 g of ethanol to provide 10.4 g of triethylmethylammonium perchlorate (yield of 82.7% to triethylamine).

EXAMPLE 2

(1st Step)

In a stirring system autoclave were filled 68.8 g of dimethyl carbonate, 65.0 g of N-methylpyrrolidine, and 60.0 g of methanol as solvent and they were reacted for 6 hours at reaction temperature of 120° C. and reaction pressure of 3 kg/cm$^2$G. After the reaction, the autoclave was cooled and then the reaction mixture was collected and analyzed. The results showed that the conversion of N-methylpyrrolidone was 98.1%. When unreacted materials and the solvent were distilled off, 130.6 g of solids were recovered (97.6% of the theoretical value). From the elemental analysis and H-NMR thereof, the solids were confirmed to be N,N-dimethylpyrrolidinium methyl carbonate.

(2nd Step)

By following the same procedure (2nd step) of Example 1 except that 10.0 g of N,N-dimethylpyrrolidinium methyl carbonate thus obtained and 12.9 g of an aqueous solution of 42% HBF$_4$ were used, 10.1 g (yield of 92.4% to N-methylpyrrolidine) of high-pure dimthylpyrrolidinium tetrafluoroborate was obtained.

EXAMPLE 3

By gradually adding 5.7 g of HSO$_3$F to 10.0 g of N,N-dimethylpyrrolidinium methyl carbonate obtained in Example 2 (1st Step) and removing carbon dioxide generated at 50° C./5 mmHg, 10.8 g (yield of 92.7% to N-methylpyrrolidine) of dimethylpyrrolidinium fluorosulfate was obtained.

EXAMPLE 4

(1st Step)

By following the same procedure as Example 1 (1st step) except that 8.8 g of dimethyl carbonate, 10.0 g of pyridine, and 10.0 g of methanol as solvent were used, 16.8 g (78.5% of the theoretical yield) of solids were obtained. The solid was confirmed to be N-methylpyridinium methyl carbonate.

(2nd Step)

By following the same procedure as Example 1 (2nd step) except that 10.0 g of n-methylpyridinium methyl carbonate and 9.9 g of 60% HClO$_4$ were used, 10.8 g (yield of 74.3% to pyridine) of N-methylpyridinium perchlorate was obtained.

EXAMPLE 5 (1st Step)

By following the same procedure as Example 1 (1st step) except that 17.0 g of dimethyl carbonate and 10.0 g of 1,5-diazabicyclo[4,3,0]-5-nonene were used as the raw materials, 12.6 g (72.8% of the theoretical yield) of a viscous liquid was obtained. From the elemental analysis, $^1$H-NMR, MS, etc., the viscous liquid was confirmed to be 1-methyl-1-azonia- 5-azabicyclo[4,3,0]-5-nonene methyl carbonate.

(2nd Step)

By following the same procedure as Example 1 (2nd step) except that 8.0 g of 1-methyl-1-azonia-5-azabicyclo-[4,3,0]-5-nonene methyl carbonate and 7.4 g of 40% HBF$_4$, 8.2 g (yield of 70.8% to 1,5-diazabicyclo[4,3,0]-5-nonene) of 1-methyl-1-azonia-5-azabicyclo[4,3,0]-5-nonene tetrafluoroborate was obtained.

EXAMPLE 6

In 10.0 g of water was dissolved 4.5 g of triethylmethylammonium methyl carbonate obtained by the same manner as in Example 1 (1st step) and a solution of 2.7 g of maleic acid dissolved in 20.0 g of water was gradually added to the solution, whereby carbon dioxide generated vigorously. For more completely removing carbon dioxide, degassing was performed for 2 hours at 40° C. and 20 mmHg. After confirming the carbonate ions being less than 20 ppm by ion chromatography, water was distilled off. The residue formed was recrystallized from methyl ethyl ketone to provide 3.1 g (yield of 84.4% to triethylamine) of high-pure mono-triethylmethylammonium maleate. The ion analysis of mono-triethylmethylammonium maleate thus obtained confirmed that impurities such as $Cl^-$, $Br^-$, $SO_4^{2-}$, $NO_3^-$, etc., were all less than 1 ppm and the product was a very high-pure salt.

EXAMPLE 7

By following the same procedure as Example 6 except that 8.3 g of N,N-dimethylpyrrolidinium methyl carbonate obtained as in Example 2 (1st step) was used, 12.7 g (yield of 88.5% to N-methylpyrrolidine) of dimethylpyrrolidinium monoadipate was obtained.

EXAMPLE 8

By following the same procedure as Example 7 except that 10.0 g of N,N-dimethylpyrrolidinium methyl carbonate and 5.4 g of phenol were used, 10.7 g (yield of 94.7% to N-methylpyrrolidine) of dimethylpyrrolidinium phenolate was obtained.

EXAMPLE 9

By following the same procedure as Example 6 except that 10.0 g of N-methylpyridinium methyl carbonate obtained in the 1st step of Example 4 and 3.1 g of acetic acid were used, 8.7 g (yield of 75.4% of pyridine) of N-methylpyridinium acetate was obtained.

EXAMPLE 10

By following the same procedure as Example 6 except that a mixture of N-methylpyridinium methyl carbonate obtained in the 1st step of Example 4 and an equimolar amount of maleic acid were used, 4-methylpyridinium maleate was synthesized. By recrystallization, the desired product was obtained at 96.0% of the theoretical yield (yield of 75.4% to pyridine).

EXAMPLE 11

By following the same procedure as Example 6 except that 8.0 g of 1-methyl-1-azonia-5-azabicyclo[4,3,0]-5nonenemethyl carbonate obtained as in the 1st step of Example 6, 8.7 g (yield of 66.7% to 1,5-diazabicyclo[4,3,0]-5nonene) of 1-methyl-1-azonia-5-azabicyclo[4,3,0]-5-nonene maleate was obtained.

EXAMPLE 12

(1st Step)

In a stirring system autoclave were filled 9.0 g of dimethyl carbonate and 18.5 g of tri-n-butylphosphine and they were reacted for 15 hours at reaction temperature of 115° C. and reaction pressure of 5.0 kg/cm². After the reaction was over, the autoclave was cooled and then the reaction mixture was collected and analyzed by gas chromatography. The conversion of the tri-n-butylphosphine was 72.8% and the amount of the solid product after distilling off the unreacted materials and the solvent was 17.5 g (63.6% of the theoretical yield). From the elemental analysis and $^1$H-NMR, the solid product was confirmed to be tri-n-butylmethylphosphonium carbonate.

(2nd Step)

In 10.0 g of water was dissolved 10.0 g of tri-n-butylmethylphosphonium carbonate and 7.9 g of an aqueous solution of 42% $HBF_4$ was gradually added to the solution, whereby carbon dioxide simultaneously generated vigorously. For more completely removing carbon dioxide from the system, degassing was performed for 2 hours at 40° C. and 20 mmHg and after confirming carbon dioxide being less than 20 ppm, water was distilled off. The residue formed was recrystallized from a mixture of water and methanol to provide 10.1 g (92.4% of the theoretical yield, yield of 58.8% to tri-n-butylphosphine) of tri-n-butylmethylphosphonium tetrafluoroborate.

EXAMPLE 13

(1st Step)

By following the same procedure as the 1st step of Example 12 except that 9.0 g of dimethyl carbonate, 11.8 g of triethylphosphine, and 10.0 g of methanol as solvent were used, 17.2 g (78.9% of the theoretical yield) of a solid product was obtained. From the elemental analysis and $^1$HNMR, the solid product was confirmed to be triethylmethylphosphonium carbonate.

(2nd Step)

By following the same procedure as the 2nd step of Example 12 except that 10.0 g of triethylmethylphosphonium carbonate, 11.3 g of an aqueous solution of 42% $HBF_4$, and 10.0 g of water, 10.8 g (95.3% of the theoretical yield, yield of 79.2% to triethylphosphine) of triethylmethylphosphonium tetrafluoroborate was obtained.

EXAMPLE 14

(1st Step)

By following the same procedure as the 1st step of Example 12 except that 9.0 g of dimethyl carbonate, 17.8 g of 1-phenylphosphane, and 10.0 g of methanol as solvent were used, 19.1 g (71.3% of the theoretical yield) of a solid product was obtained. From the elemental analysis and $^1$H-NMR, the solid product was confirmed to be 1-methylphenylphosphanium carbonate. (2nd Step)

By following the same procedure as the 2nd step of Example 12 except that 10.0 g of 1-methylphenylphosphanium carbonate, 6.9 g of 60% perchlorate, and 10.0 g of water were used, 10.9 g (94.8% of the theoretical yield, yield of 67.6% to 1-phenylphosphane) of methylphosphanium perchlorate was obtained.

EXAMPLE 15

(1st Step)

By following the same procedure as the 1st step of Example 12 except that 9.0 g of dimethyl carbonate, 21.2 g of triphenylphosphine, and 10.0 g of methanol as solvent were used, 21.3 g (60.5% of the theoretical yield) of a solid product was obtained. From the elemental analysis and $^1$H-NMR, the solid product was confirmed to be triphenylmethylphosphonium carbonate.

(2nd Step)

By following the same procedure as the 2nd step of Example 12 except that 10.0 g of triphenylmethylphosphonium carbonate, 6.2 g of 60% prechlorate, and 100 g of ethanol as solvent were used, 10.3 g (92.8% of the theoretical yield, yield of 56.1% to triphenylphosphine) of triphenylmethylphosphonium perchlorate was obtained.

EXAMPLE 16

In 10.0 g of water was dissolved 10.0 g of tri-n-butylmethylphosphonium carbonate obtained as in Example 12 (1st step) and a solution of 4.2 g of maleic acid dissolved in 5.0 g of water was gradually added to the solution, whereby carbon dioxide simultaneously generated vigorously. For more completely removing carbon dioxide, degassing was performed for 2 hours at 40° C. and 20 mmHg and after confirming carbonate ions being less than 2 ppm, water was distilled off. The residue formed was recrystallized from methyl ethyl ketone to produce 1–1.2 g (94.1% of the theoretical yield, yield of 59.8% to tri-n-butylphosphine) of tri-n-butylmethylphosphonium monomaleate.

EXAMPLE 17

By following the same procedure as Example 16 except that 10.0 g of triethylmethylphosphonium carbonate obtained in Example 1 (1st step), 7.5 g of adipic acid, and 10.0 g of water, 13.5 g (94.4% of the theoretical yield, yield of 74.5% to triethylphosphine) of triethylmethylphosphonium monoadipate was obtained.

EXAMPLE 18

By following the same procedure as Example 16 except that 10.0 g 1-methylphenylphosphanium carbonate obtained as in the 1st step of Example 14, 3.7 g of phenol, and 10.0 g of water were used, 10.2 g (90.3% of the theoretical yield, yield of 64.4% to 1-phenylphosphane) of 1-methylphenylphosphanium phenolate was obtained.

EXAMPLE 19

By following the same procedure as Example 16 except that 10.0 g of triphenylmethylphosphonium carbonate obtained as in the 1st step of Example 15, 1.8 g of acetic acid, and 10.0 g of water, 9.6 g (96.6% of the theoretical yield, yield of 58.4% to triphenylphosphine) of triphenylmethylphosphonium acetate was obtained.

EXAMPLE 20

(1st Step)

In a stirring system autoclave were filled 67.5 g of dimethyl carbonate, 36.9 g of trimethylamine, and 90.0 g of methanol as solvent and they were reacted for 3 hours at reaction temperature of 110° C. and reaction pressure of 6 kg/cm$^2$G. The amount of the solid product after distilling off the unreacted materials and the solvent was 100.2 g (96% of the theoretical yield). From the elemental analysis and $^1$H-NMR, the solid product was confirmed to be tetramethylammonium methyl carbonate. (2nd Step)

In a 500 milliliter three neck distillation flask equipped with a thermometer and a condenser, 53.2 g of tetramethylammonium methyl carbonate was dissolved in 53.2 g of water and while refluxing the solution for one hour at 40° C. and 20 mmHg, methanol was distilled off. When the reaction mixture was collected and analyzed by gas chromatography, the content of methanol was less than 0.01%. When 52.8 g of phthalic anhydride was added to the solution followed by stirring at 50° C., carbon dioxide generated vigorously. After one hour since then, all unreacted phthalic anhydride was dissolved and forming by carbon dioxide was stopped to provide a transparent solution. For more completely removing carbon dioxide from the system, degassing was performed for one hour at 40° C. and 20 mmHg, water was distilled off to provide 85.2 g (yield of 99.9% to tetramethylammonium methyl-carbonate) of a white solid product. From the elemental analysis, $^1$H-NMR, and the liquid chromatography, it was confirmed that the solid product was mono-tetramethylammonium phthalate and the content of monomethyl phthalate was less than 0.1%. The ion analysis of mono-tetramethylammonium phthalate obtained confirmed that the contents of impurities such as Cl$^-$, Br$^-$, SO$_4^{2-}$, NO$_3^-$, etc., were all less than 1 ppm and the product was a very high-purity salt.

COMPARATIVE EXAMPLE

In a 500-milliliter three neck distillation flask equipped with a thermometer and a condenser, 50.5 g of tetramethylammonium methyl-carbonate was dissolved in 50.5 g of water and then 50.1 g of phthalic anhydride was added to the solution followed by stirring at 50° C., whereby carbon dioxide generated vigorously. After one hour since then, all unreacted phthalic anhydride was dissolved and the forming by carbon dioxide was stopped to provide a colorless transparent solution. For more completely removing carbon dioxide from the system, degassing was performed for one hour at 40° C. and 20 mmHg and then water was distilled off to provide 83.5 g of a white solid product. From $^1$H-NMR and liquid chromatography, it was confirmed that the white solid product obtained contained 8.9% monomethyl phthalate in addition to mono-tetramethylammonium phthalate.

EXAMPLE 21

By following the same procedure as Example 20 (2nd step) except that 17.5 g of N,N-dimethylpyrrolidinium methyl carbonate, 17.5 g of water, and 9.8 g of maleic anhydride were used, 21.4 g (yield of 99.6%) of N,N-dimethylpyrrolidinium maleate was obtained. The content of mono-maleate was less than 0.1% and the contents of impurity ions were less than 1 ppm.

EXAMPLE 22

By following the same procedure as Example 20 (2nd step) except that 8.8 g of methyltriethylammonium methyl carbonate, 8.8 g of water, and 4.5 g of maleic anhydride were used, 10.6 g (yield of 100%) of methyltriethylammonium maleate was obtained. The content of monomethyl maleate was less than 0.15 and the contents of impurity ions were all less than 1 ppm.

EXAMPLE 23

(1st Step)

By following the same procedure as Example 1 (1st step) except that 24.6 g of dimethyl carbonate, 2.0 g of ethyldimethylamine, and 20.0 g of methanol as solvent were used, 43.9 g (yield of 98.4% to ethyldimethylamine) was obtained.

(2nd Step)

By following the same procedure as Example 20 (2nd step) except that 7.8 g of ethyltrimethylammonium methyl carbonate, 7.8 g of water, and 4.7 g of maleic anhydride were used, 9.7 g (yield of 99.9%) of ethyltrimethylammonium maleate was obtained. The content of monomethyl maleate was less than 0.1% and the contents of impurity ions were all less than 1 ppm.

EXAMPLE 24

(1st Step)

By following the same procedure as Example 1(1st step) except that 13.4 g of dimethyl carbonate, 15.0 g of N-methylmorpholine, and 15.0 g of methanol as solvent were used, 23.9 g (yield of 84.3% to N-methylmorpholine) of N,N-dimethylmorpholinium methyl carbonate was obtained.

(2nd Step)

By following the same procedure as Example 20 (2nd step) except that 19.1 g of N,N-dimethylmorpholinium methyl carbonate, 19.1 g of water, and 9.8 g of maleic anhydride were used, 23.0 g (yield of 99.9%) of N,N-dimethylmorpholinium maleate was obtained. The content of monomethyl maleate was less than 0.1% and the contents of impurity ions were all less than 1 ppm.

EXAMPLE 25

(1st Step)

By following the same procedure as Example 1 (1st step) except that 7.3 g of dimethyl carbonate, 8.0 g of N-methylpiperidine, and 8.0 g of methanol as solvent were used, 11.1 g (82.4% to N-methylpiperidine) of N,N-dimethylpiperidinium methyl carbonate was obtained.

(2nd Step)

By following the same procedure as Example 20 (2nd step) except that 18.9 g of N,N-dimethylpiperidinium methyl carbonate, 18.9 g of water, and 9.8 g of maleic anhydride were used, 22.9 g (yield of 100%) of N,N-dimethylpiperidinium maleate was obtained. The content of monomethyl maleate was less than 0.1% and the content of impurity ions were all less than 1 ppm.

EXAMPLE 26

By following the same procedure as Example 21 except that 11.2 g of citraconic anhydride was used in place of maleic anhydride in Example 21, 22.8 g (yield of 99.6%) of N,N-dimethylpyrrolidinium citraconate was obtained. The content of monomethyl citraconate was less than 0.1% and the contents of impurity ions were all less than 1 ppm.

While the invention has been described in detail and with reference to specific embodiments thereof, it will be apparent to one skilled in the art that various changes and modifications can be made therein without departing from the spirit and scope thereof.

What is claimed is:

1. A process for producing a quaternary salt comprising
   (a) a first step of reacting (a1) one number selected from the group consisting of tertiary alkylamines, N,N,N',N'-tetramethylethylenediamine, N-alkylpyrrolidines, N-alkylpiperidines, N-alkylhexamethyleneimines, N-alkylmorpholines, N,N'-dialkylpiperazines, 1,5-diazabicyclo[4,3,0]-5-nonene, 1,8-diazabicyclo[5,4,0]-7-undecene, alkylpyridines, 4-dimethylaminopyridine, picoline, N-alkylimidazoles, N-methylbenzimidazole, quinoline, 4,4,-dipyridyl, trialkylphosphines, tricyclohexylphosphine, 1,2-bis(dimethylphosphine)ethane, triphenylphosphine, tribenzylphosphine, dialkylphenylphosphines, alkyl-diphenylphosphine, 1-ethylphosphoran, 1-phenylphosphoran, 1-phenylphosphane, and 1-phenylphosphate, with (a2) a carbonic acid dialkylester at a temperature of 20° C. to 200° C. to produce a corresponding quaternary carbonate, and
   (b) a second step of mixing the quaternary carbonate thus formed with an acid or an acidic phenol, while removing carbon dioxide generated from the system, to replace the carbonate anion with the corresponding acid or phenyl anion.

2. The process as claimed in claim 1, wherein the mol ratio of the tertiary amine or phosphine to the carbonic acid diester, is from 0.2 to 5.

3. The process as claimed in claim 1, wherein a stoichiometric amount or a little excess amount of the acid is added dropwise to the quaternary carbonate formed.

4. The process as claimed in claim 1, wherein the acid being mixed with the quaternary carbonate is an organic acid.

5. The process as claimed in claim 1, wherein the carbonic said diester is dimethyl carbonate.

6. A process for producing a quaternary salt comprising
   (a) a first step of reacting (a1) one member selected from the group consisting of tertiary alkylamines, N,N,N',N'-tetramethylethylenediamine, N-alklpyrrolidines, N-alkylpiperdines, N-alkylhexamethyleneimines, N-alkylmorpholines, N,N'-dialkylpiperazines, 1,5-diazabicyclo[4,3,0]-5-nonene, 1,8-diazabicyclo[5,4,0]-7-undecene, alkylpyridines, 4-dimethylaminopyridine, picoline, N-alklimidazoles, N--methylbenzimidazole, quinoline, 4,4'-dipyridyl, trialkylphosphines, tricyclohexylphosphine, 1,2-bis(dimethylphosphine)ethane, triphenylphosphine, tribenzylphosphine, dialkylphenylphosphines, alkyl-diphenylphosphine, 1-ethylphosphoran, 1-phenylphosphoran, 1-phenylphosphane, and 1-phenylphosphetane, with (a2) a carbonic acid dialkyl-ester at a temperature of 20° C. to 200° C. to produce a corresponding quaternary carbonate, and
   (b) a 2nd step of dissolving the quaternary carbonate in water and after removing methonal formed from the system, mixing the solution with a carboxylic acid anhydride while removing carbon dioxide generated from the system.

7. The process as claimed in claim 6, wherein water is used in an amount of 0.1 to 100 parts by weight to one part by weight of the quaternary carbonate.

8. The process as claimed in claim 6, wherein the carboxylic acid anhydride is a dibasic acid.

* * * * *